(12) United States Patent
Williams et al.

(10) Patent No.: US 9,326,809 B2
(45) Date of Patent: May 3, 2016

(54) ELECTROSURGICAL APPARATUS AND SYSTEM

(71) Applicant: GYRUS MEDICAL LIMITED, Cardiff (GB)

(72) Inventors: Wayne Williams, Penarth (GB); Teo Heng Jimmy Yang, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 249 days.

(21) Appl. No.: 13/644,232

(22) Filed: Oct. 3, 2012

(65) Prior Publication Data
US 2013/0090644 A1 Apr. 11, 2013

(30) Foreign Application Priority Data
Oct. 6, 2011 (GB) .................................. 1117274.9

(51) Int. Cl.
*A61B 18/14* (2006.01)
*A61B 18/04* (2006.01)
*A61B 18/00* (2006.01)

(52) U.S. Cl.
CPC ..... *A61B 18/042* (2013.01); *A61B 2018/00589* (2013.01)

(58) Field of Classification Search
CPC ............... A61B 2018/00589; A61B 18/042; A61B 18/14; A61B 2018/1472; A61B 2018/00065; A61B 2018/00029
USPC ................................................ 606/33, 40–52
See application file for complete search history.

(56) References Cited

U.S. PATENT DOCUMENTS

| 4,040,426 | A | | 8/1977 | Morrison, Jr. | |
| 5,720,745 | A | * | 2/1998 | Farin et al. | 606/49 |
| 6,039,736 | A | | 3/2000 | Platt, Jr. | |
| 6,197,026 | B1 | | 3/2001 | Farin et al. | |
| 6,616,660 | B1 | * | 9/2003 | Platt | 606/49 |
| 7,537,595 | B2 | * | 5/2009 | McClurken | 606/50 |
| 8,083,736 | B2 | * | 12/2011 | McClurken et al. | 606/41 |
| 8,460,283 | B1 | * | 6/2013 | Laroussi | A61B 18/042 315/111.21 |

(Continued)

FOREIGN PATENT DOCUMENTS

| WO | WO 2006/084316 A1 | 8/2006 | |
| WO | WO 2011/022069 A2 * | 2/2011 | A61B 18/04 |

OTHER PUBLICATIONS

Jan. 10, 2012 Search Report issued in British Patent Application No. GB1117274.9.

(Continued)

*Primary Examiner* — Michael Peffley
*Assistant Examiner* — Thomas Giuliani
(74) *Attorney, Agent, or Firm* — Oliff PLC

(57) ABSTRACT

An electrosurgical apparatus for coagulating tissue comprises an elongate tube (3) having a proximal end and a distal end, and having a distal end face (12). The tube comprises one or more first apertures (14) located at the distal end face (12) and one or more second apertures (13) located along the periphery of the tube between the proximal and distal ends. The tube provides a conduit though which ionizable gas can be supplied to the distal end of the tube, and includes at least one electrode (4) for ionizing the ionizable gas exiting either the first or second apertures.

8 Claims, 3 Drawing Sheets

(56) References Cited

U.S. PATENT DOCUMENTS

Figure 1:
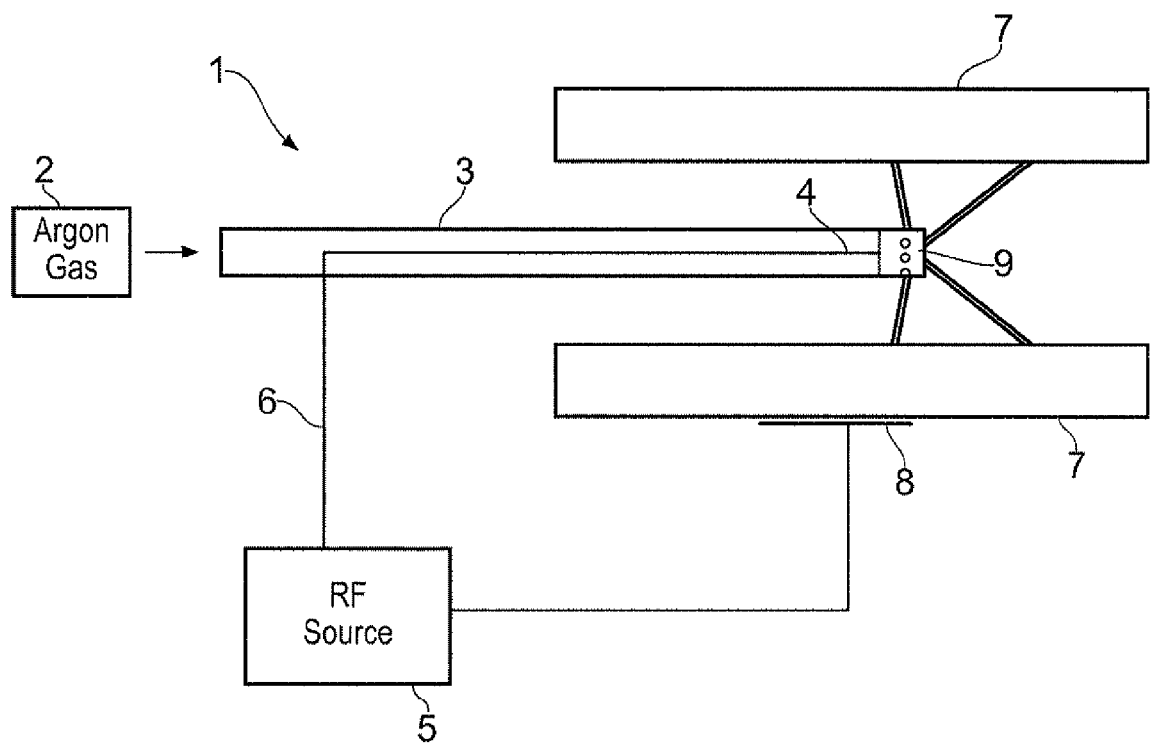

2004/0044342 A1* 3/2004 Mackay ............... 606/45
2004/0260280 A1* 12/2004 Sartor ............... 606/37
2007/0106113 A1* 5/2007 Ravo ............... 600/113
2008/0039834 A1* 2/2008 MacKay ............... A61B 18/042
  606/46

OTHER PUBLICATIONS

Jan. 4, 2013 Search Report issued in British Patent Application No. GB1217767.1.
Jan. 6, 2016 Office Action in UK Patent Application No. GB1217767.1.

* cited by examiner

ELECTROSURGICAL APPARATUS AND SYSTEM

This invention relates to an electrosurgical apparatus and system and in particular to the non-contact coagulation of tissue using an ionizable gas such as argon. Argon beam coagulators have been known for many years, and examples are given in U.S. Pat. Nos. 4,040,426, 6,039,736 and 6,197,026. The first example is an end-effect instrument, in which the ionized gas exits through the end of the instrument, while the latter two examples are directed at side-effect instruments, in which the ionized gas exits the instrument though an aperture in the side of the instrument. Such instruments are often referred to as APC instruments (Argon Plasma Coagulation).

The invention attempts to provide an instrument which is more versatile than any of the instruments in the prior art, and accordingly resides in an electrosurgical apparatus for coagulating tissue, comprising an elongate tube having a proximal end and a distal end, and having a distal end face, the tube comprising one or more first apertures located at the distal end face and one or more second apertures located along the periphery of the tube between the proximal and distal ends, a conduit through which ionizable gas can be supplied to the distal end of the tube; and at least one electrode for ionizing the ionizable gas exiting either the first or second apertures.

Previous APC instruments have either been end-effect instruments or side-effect instruments, and individual surgeons have tended to prefer one type of instrument over another. The present invention provides a hybrid APC instrument, which is capable of acting as either a side-effect or an end-effect instrument, depending on how it is deployed by the surgeon. While gas will exit from both the one or more apertures in the end face of the tube and also through the one or more apertures along the periphery of the tube, the plasma arc initiated by the one or more electrodes will tend to follow the line of lowest impedance. This will tend to be the line of shortest distance to the tissue. This means that when the peripheral aperture is closest to the tissue, an arc will be formed from the peripheral aperture to the tissue, resulting in a side-effect instrument. When a plurality of apertures is present around the periphery of the tube, the arc will be formed from the aperture or apertures closest to the tissue. Conversely, when the aperture in the end face is closest to the tissue, an arc will be formed from the end aperture to the tissue, resulting in an end-effect instrument. Similarly, when a plurality of apertures is present in the end face of the tube, the arc will be formed from the aperture or apertures closest to the tissue. In this way, the device will work as either a side-effect or an end effect instrument, merely due to the orientation of the tube with respect to the tissue.

In one convenient arrangement, the one or more first apertures comprise a single aperture present in the distal end face of the tube. Typically, the single aperture constitutes the majority of the distal end face of the tube. The aperture can conceivably constitute the whole end face of the tube, such that the tube is effectively open-ended. Alternatively, the single aperture is present in one quadrant of the end face of the tube, allowing the plasma beam to be directed more closely.

In an alternative arrangement, the instrument includes a plurality of first apertures in the distal end face of the tube. This means that the arc will be instigated from whichever aperture is closest to the surrounding tissue.

Similarly, the one or more second apertures conveniently comprise a single aperture present on the periphery of the tube. In this way, the user of the instrument will know that the device will only fire up and produce a plasma arc in a single sideways orientation. Alternatively, the apparatus includes a plurality of apertures located around the periphery of the tube. In this arrangement, the user is able to coagulate tissue located adjacent the tube in any orientation, without the need to re-orient the tube to bring a single side aperture into position. In this arrangement, the apertures are conveniently spaced around the entire circumference of the tube, preferably spaced equidistantly around the circumference of the tube.

The at least one electrode is capable of ionizing the gas exiting the apertures. The electrode can conceivably be positioned within the tube, such that the gas is formed into a plasma before it exits the apertures. Alternatively, the electrode can be positioned at the first and second apertures, such that it creates a plasma as the gas is exiting the tube. In one convenient arrangement, the apertures are formed in a metallic mesh which constitutes the electrode, such that the plasma is initiated just as the gas passes through the aperture.

The tube is conveniently flexible, such that it can be used in endoscopic surgical procedures, in which the tube is required to reach the intended surgical site via a lumen within the body of a patient. Alternatively, the tube may be rigid, in which case the instrument is more suitable for laparoscopic surgical procedures. The tube is conceivably a composite tube, with a body portion and an end-piece. The apertures may conveniently be present either in the body portion, the end-piece, or both.

In one arrangement, the apparatus includes only a single electrode for ionizing the gas, the electrical circuit being completed via a patient return pad present on the patient. This form of instrument is commonly known as a monopolar instrument. Alternatively, the instrument may conveniently be a bipolar instrument, with first and second electrodes present on the instrument. In such a bipolar instrument, the electrodes are relatively close together, and the electrical circuit is completed by the electric current flowing from one electrode to the other, through the ionizable gas. Conceivably, the electrodes could be placed further apart, with the electrical circuit being completed capacitively. The invention also resides in an electrosurgical system including an electrosurgical apparatus as previously described, together with a source for supplying ionizable gas to the proximal end of said tube, and an electrosurgical generator for supplying high frequency energy to the at least one electrode. According to a preferred arrangement, the electrosurgical generator is adapted to supply the high frequency energy in the form of a succession of pulses. This means that the plasma arc is continually extinguished and re-established, resulting in a situation in which the re-established arc can take a different path should a different aperture now present a shorter path to the tissue. Once an arc is established, the ionization presents a low impedance path which may mean that the arc is maintained in its original path, even if an alternative path is now shorter in distance to the tissue. By constantly extinguishing and re-establishing the arc in this way, the arc will easily switch to different paths as the tube is repositioned, and the tendency for the arc to maintain a certain path beyond a desired duration is avoided.

The invention further resides in a method of coagulating tissue comprising the steps of i) providing an electrosurgical apparatus consisting of an elongate tube having a proximal end and a distal end, the elongate tube having a distal end face and one or more first apertures located at the distal end face and one or more second apertures located along the periphery of the tube between the proximal and distal ends, a conduit linking the proximal and distal ends of the tube; and at least one electrode for ionizing the ionizable gas exiting either the first or second apertures, ii) supplying an ionizable gas through the conduit to the distal end of the tube, iii) supplying high frequency energy to the at least one electrode in order to ionize the gas, iv) maneuvering the electrosurgical apparatus such that the one or more first apertures are adjacent tissue to be coagulated such that an arc will be formed between the at least one electrode and the tissue such that a plasma is created between the electrode and the tissue passing through the one or more first apertures, and v) repositioning the electrosurgical apparatus such that the one or more second apertures are adjacent tissue to be coagulated such that an arc will be formed between the at least one electrode and the tissue such that a plasma is created between the electrode and the tissue passing through the one or more second apertures.

The invention also includes an electrosurgical instrument for coagulating tissue comprising an elongate tube having a proximal end portion and a distal end portion, the distal end portion having a plurality of apertures providing communication between the interior and the exterior of the tube distal end portion, a conduit arranged to be connected to a source of ionizable gas and to supply gas from the source to the interior of the tube distal end portion, and at least one electrode arranged to be connected to a radio frequency power source and to ionize the supplied gas, wherein the apertures comprise at least one distally directed end-effect aperture and a plurality of laterally directed side-effect apertures, and wherein the electrode is located so as to be capable of ionizing either the supplied gas exiting the end-effect aperture or the gas exiting a said side-effect aperture depending on the position of the tube distal end portion relative to the tissue to be coagulated.

Figure 2:
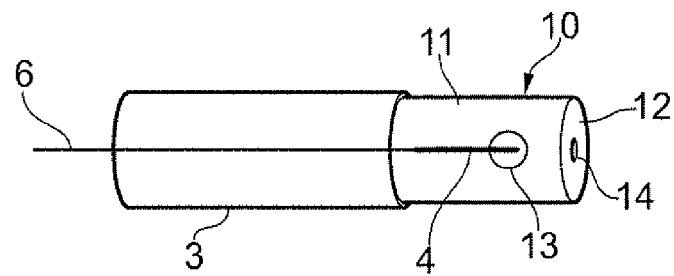
Figure 3:
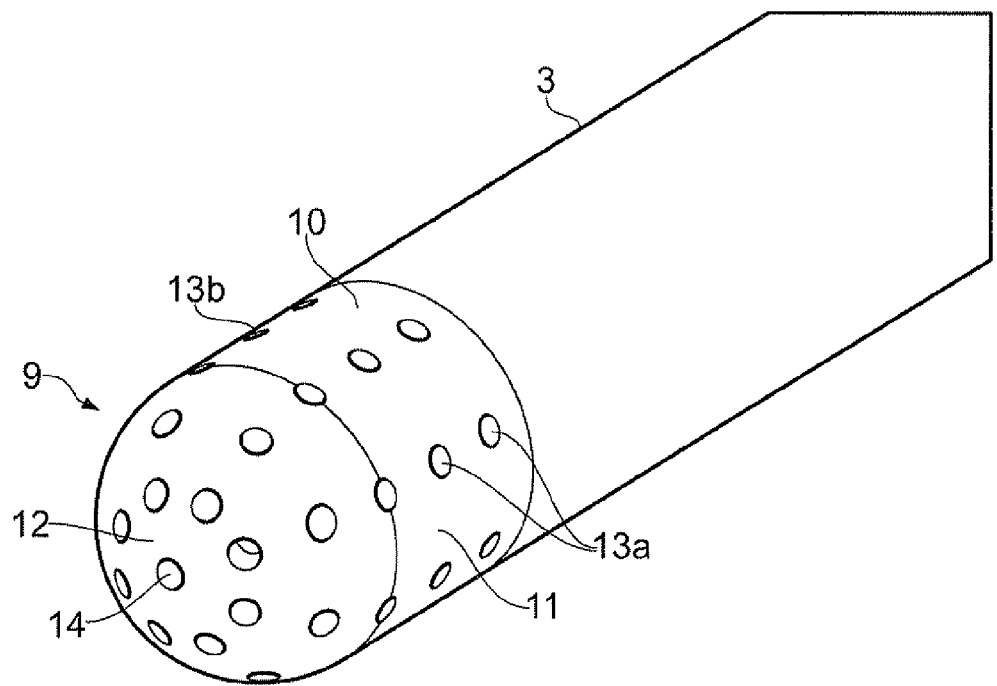
Figure 4:
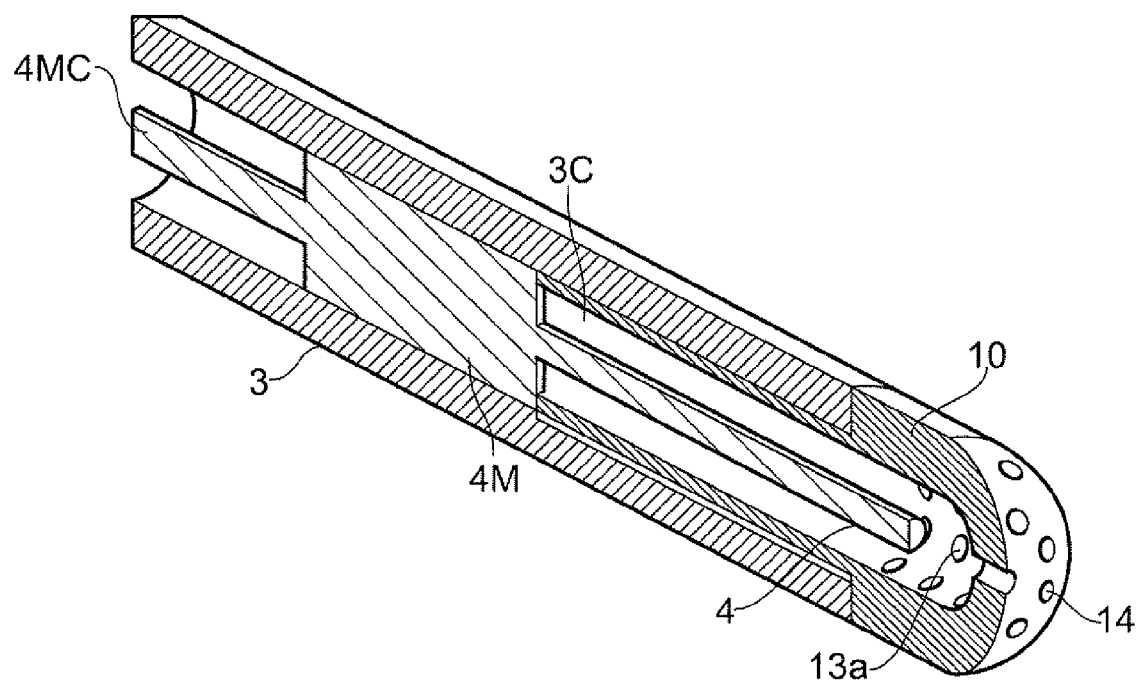
Figure 5:
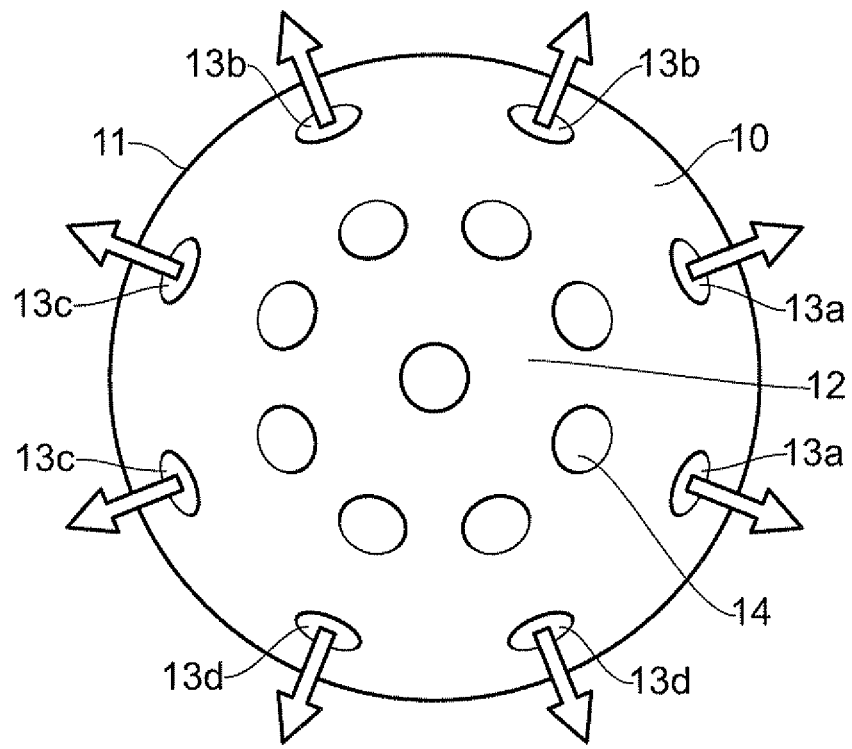
Figure 6:
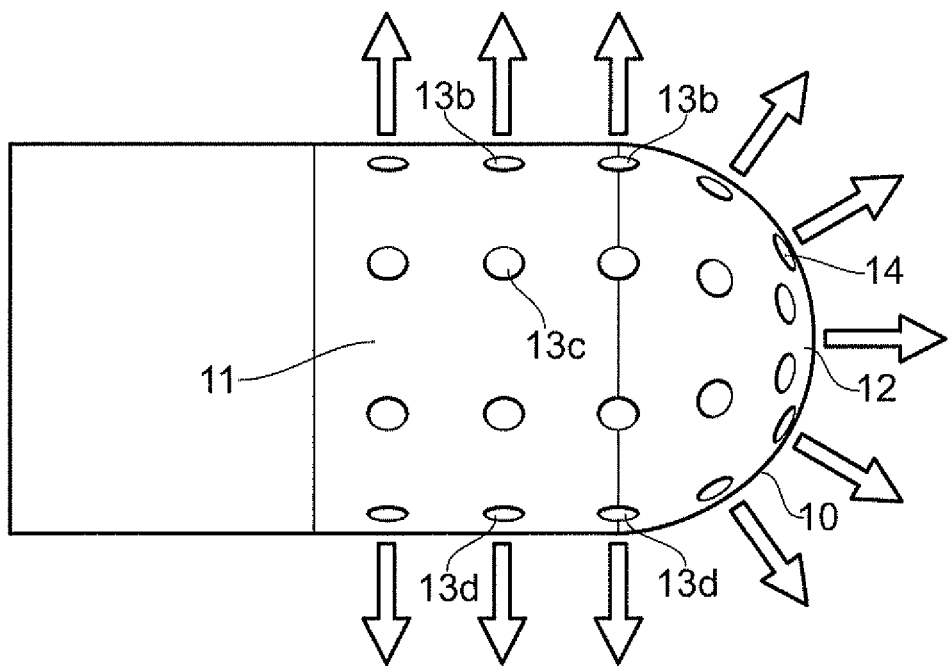

The invention will now be further described, by way of example only, with reference to the accompanying drawings, in which:

FIG. 1 is a schematic view of an electrosurgical system in accordance with the present invention, FIG. 2 is a schematic perspective view of the tip of an electrosurgical instrument used as part of the electrosurgical system of FIG. 1, FIG. 3 is a perspective view of the tip of an alternative embodiment of electrosurgical instrument in accordance with the present invention, FIG. 4 is a schematic sectional view of the electrosurgical instrument of FIG. 3, FIG. 5 is an end view of the electrosurgical instrument of FIG. 3, and FIG. 6 is a side view of the electrosurgical instrument of FIG. 3.

Referring to FIG. 1, an APC system comprises an instrument shown generally at 1, connected to a source 2 of argon gas. The instrument comprises a tube 3 containing a needle electrode 4, connected to a radio frequency generator 5 by means of cable 6. The instrument is shown schematically in position adjacent tissue 7, to which is connected a patient return pad 8, connecting the tissue to the generator 5. The interior of the tube 3 constitutes a gas conduit and, at a distal end portion, the tube 3 is provided with apertures, shown generally at 9, through which the argon gas supplied via the conduit can exit the tube. In use, the gas flows down the tube over the electrode 4, which causes the gas to ionize and form a plasma, which exits the apertures 9 and impinges on the tissue 7, thereby coagulating it.

The tip of the instrument 1 is shown in more detail in FIG. 2. The tube 3 is provided with a ceramic end-piece 10, having a cylindrical wall 11, and an end face 12. The wall 11 is provided with a peripheral aperture 13, while the end face 12 is provided with an end aperture 14. The electrode 4 is shown within the end-piece 10, and is connected to the generator as previously described. Argon gas flows over the electrode 4 and out of the apertures 13 and 14, and the formation of a plasma will now be described in further detail.

In order for a plasma to be formed, the distance between the electrode and the tissue must be short enough for an arc to be able to bridge the gap. If the instrument is not near tissue, then no arc (and hence no plasma) will be formed. If the instrument is brought close to tissue, then an arc will be formed through the gas flowing from one of the apertures to the tissue. If the side aperture 13 is closer to the tissue 7 as compared with the end aperture 14, then the arc will be formed through the side aperture 13, and the gas flowing through the side aperture 13 will be formed into a plasma. The instrument will therefore act as a side-effect instrument, with tissue adjacent the side aperture 13 being coagulated.

Alternatively, if the end aperture 14 is closer to the tissue 7 as compared with the side aperture 13, then the arc will be formed through the end aperture 14, and the gas flowing through the end aperture 14 will be formed into a plasma. The instrument will therefore act as an end-effect instrument, with tissue adjacent the end aperture 14 being coagulated. Thus, the user of the instrument 1 can determine whether the instrument acts as a side-effect or an end-effect instrument, by manipulating the instrument and changing its orientation and the distance of each of the apertures to the tissue 7.

FIGS. 3 to 6 show an alternative instrument in which the ceramic end-piece 10 is provided with a plurality of apertures, some in the side wall 11 and some in the end face 12. The apertures are spaced such that they are equidistant, and extend around the entire circumference of the wall 11. In this embodiment of the invention, the needle electrode 4 is formed as an axial extension of a conductive mounting plate 4M supported by the wall of the tube 3 so as to lie on the tube axis, whereby passages are formed on each side of the plate 4M to act as the conduit 3C for ionizable gas. Accordingly, argon gas supplied to a proximal end portion of the tube 3 flows on either side of the mounting plate 4M and its connection 4MC to the generator, then over the electrode 4 and subsequently out of all of the apertures 9. However, the formation of a is plasma will once again depend on the distance between the electrode 4 and the tissue 7, as previously described.

Suppose that the instrument is maneuvered such that the side apertures 13*a* on one side of the tube 3 are closer to the tissue as compared with the end apertures 14 or the side apertures 13*b*, 13*c*, 13*d* disposed in other directions around the circumference of the tube. The gas exiting the apertures 13*a* will be formed into a plasma by the electrode 4, and tissue adjacent the apertures 13*a* will be coagulated. Should the instrument be moved such that the side apertures 13*b* on another side of the tube are closer to the tissue 7 as compared with the end apertures 14 or the side apertures 13*a*, 13*c* or 13*d*, then the gas exiting the apertures 13*b* will be formed into a plasma by the electrode 4, and tissue adjacent the apertures 13*b* will be coagulated. In this way, the instrument is capable of coagulating tissue in whichever orientation the instrument 1 is brought adjacent to the tissue, whether it be one side or another (13*a* versus 13*c* for example) or adjacent the end of the instrument, using apertures 14. There is no need for the surgeon to continually re-orientate the instrument, as with some prior art devices—the user merely brings the instrument adjacent the tissue in whichever orientation is preferred, and the plasma will be instigated accordingly.

Those skilled in the art will appreciate that other constructions can be envisaged without departing from the scope of the present invention. For example, instead of using a ceramic end-piece 10 as shown, the end-piece can be electrically conductive such that it constitutes the electrode 4. In this way, the plasma is initiated as it passes through the apertures 9, provided the distance to the tissue is small enough to maintain it. Other variations such as apertures of different shapes and sizes can be envisaged, as long as the basic idea of an automatically adjusting side or end effect instrument is maintained.

The invention claimed is:

1. A method of coagulating tissue comprising the steps of:
    i) providing an electrosurgical apparatus comprising an elongate tube having a proximal end, a distal end, a distal end face, one or more first apertures located at the distal end face, one or more second apertures located along a periphery of the tube between the proximal end and the distal end, a conduit linking the proximal end and the distal end of the tube, and at least one electrode,
    ii) supplying an ionizable gas through the conduit to the distal end of the tube,
    iii) supplying high frequency energy to the at least one electrode in order to ionize the gas,
    iv) maneuvering the electrosurgical apparatus such that, when the one or more first apertures are closer to the tissue to be coagulated than the one or more second apertures, an arc is formed between the at least one electrode and the tissue such that a plasma is created between the at least one electrode and the tissue, the plasma passing through the one or more first apertures, and
    v) repositioning the electrosurgical apparatus such that, when the one or more second apertures are closer to the tissue to be coagulated than the one or more first apertures, an arc is formed between the at least one electrode and the tissue such that a plasma is created between the at least one electrode and the tissue, the plasma passing through the one or more second apertures.

2. An electrosurgical instrument for coagulating tissue comprising:
    an elongate tube having a proximal end portion and a distal end portion, the distal end portion having a plurality of apertures providing communication between an interior and an exterior of the distal end portion;
    a conduit arranged to be connected to a source of ionizable gas and to supply gas from the source to the interior of the distal end portion; and
    at least one electrode arranged to be connected to a radio frequency power source and to ionize the supplied gas; wherein
        the plurality of apertures comprise at least one distally directed end-effect aperture and a plurality of laterally directed side-effect apertures, and
        the at least one electrode is located so as to be capable of ionizing either the supplied gas exiting the at least one distally directed end-effect aperture or the gas exiting at least one of the plurality of laterally directed side-effect apertures depending on a position of the distal end portion relative to the tissue to be coagulated.

3. The electrosurgical instrument according to claim 2, wherein the distal end portion has a flat distal end face.

4. The electrosurgical instrument according to claim 2, wherein the distal end portion has a domed distal end face.

5. The electrosurgical instrument according claim 2, wherein the at least one electrode comprises a needle electrode located inside the elongate tube and extending into the interior of the distal end portion.

6. The electrosurgical instrument according to claim 2, wherein at least a section of the distal end portion is conductive and constitutes the at least one electrode.

7. The electrosurgical instrument according to claim 2, wherein the plurality of side-effect apertures are circumferentially distributed around the tube distal end portion.

8. An electrosurgical system including an electrosurgical generator having a radio frequency energy output, a source of ionizable gas and the electrosurgical instrument according to claim 2, wherein the at least one electrode is connected to the generator output and the conduit is connected to the gas source.

* * * * *